(12) United States Patent
Grichnik

(10) Patent No.: US 7,584,166 B2
(45) Date of Patent: Sep. 1, 2009

(54) EXPERT KNOWLEDGE COMBINATION PROCESS BASED MEDICAL RISK STRATIFYING METHOD AND SYSTEM

(75) Inventor: Anthony J. Grichnik, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 352 days.

(21) Appl. No.: 11/495,555

(22) Filed: Jul. 31, 2006

(65) Prior Publication Data

US 2007/0094048 A1   Apr. 26, 2007

Related U.S. Application Data

(63) Continuation-in-part of application No. 11/257,341, filed on Oct. 25, 2005, now Pat. No. 7,487,134.

(51) Int. Cl.
*G06F 15/00* (2006.01)
*G06F 15/18* (2006.01)

(52) U.S. Cl. ......... 706/62
(58) Field of Classification Search ......... None
See application file for complete search history.

(56) References Cited

U.S. PATENT DOCUMENTS

| | | |
|---|---|---|
| 3,316,395 A | 4/1967 | Lavin |
| 4,136,329 A | 1/1979 | Trobert |
| 4,533,900 A | 8/1985 | Muhlberger et al. |
| 5,014,220 A | 5/1991 | McMann et al. |
| 5,163,412 A | 11/1992 | Neu et al. |
| 5,262,941 A | 11/1993 | Saladin et al. |

(Continued)

FOREIGN PATENT DOCUMENTS

EP   1103926   5/2001

(Continued)

OTHER PUBLICATIONS

Multicategory Prediction of Multifactorial Diseases Through Risk Factor Fusion and Rank-Sum Selection Phegley, J.W.; Perkins, K.; Gupta, L.; Hughes, L.F.; Systems, Man and Cybernetics, Part A, IEEE Transactions on vol. 35, Issue 5, Sep. 2005 pp. 718-726 Digital Object Identifier 10.1109/TSMCA.2005.843390.*

(Continued)

*Primary Examiner*—Michael B Holmes
(74) *Attorney, Agent, or Firm*—Finnegan, Henderson, Farabow, Garrett & Dunner

(57) ABSTRACT

A method is provided for a medical risk stratification system. The method may include obtaining data records associated with one or more health variables and a plurality of medical risks from a plurality of MRS models based on an expert knowledge combination process and establishing a medical risk process model indicative of interrelationships between the plurality of medical risks and a plurality of health parameters based on the data records. The method may also include obtaining a set of values corresponding to the plurality of health parameters and calculating values of the plurality of medical risks simultaneously based upon the set of values corresponding to the plurality of health parameters and the medical risk process model. Further, the method may include optimizing the plurality of health parameters to minimize the plurality of medical risks simultaneously and presenting the values of the plurality of medical risks.

19 Claims, 8 Drawing Sheets

U.S. PATENT DOCUMENTS

| | | | |
|---|---|---|---|
| 5,341,315 A | 8/1994 | Niwa et al. |
| 5,386,373 A | 1/1995 | Keeler et al. |
| 5,434,796 A | 7/1995 | Weininger |
| 5,539,638 A | 7/1996 | Keeler et al. |
| 5,548,528 A | 8/1996 | Keeler et al. |
| 5,561,610 A | 10/1996 | Schricker et al. |
| 5,566,091 A | 10/1996 | Schricker et al. |
| 5,585,553 A | 12/1996 | Schricker |
| 5,594,637 A | 1/1997 | Eisenberg et al. |
| 5,598,076 A | 1/1997 | Neubauer et al. |
| 5,604,306 A | 2/1997 | Schricker |
| 5,604,895 A | 2/1997 | Raimi |
| 5,608,865 A | 3/1997 | Midgely et al. |
| 5,666,297 A | 9/1997 | Britt et al. |
| 5,682,317 A | 10/1997 | Keeler et al. |
| 5,698,780 A | 12/1997 | Mizutani et al. |
| 5,727,128 A | 3/1998 | Morrison |
| 5,750,887 A | 5/1998 | Schricker |
| 5,752,007 A | 5/1998 | Morrison |
| 5,835,902 A | 11/1998 | Jannarone |
| 5,842,202 A | 11/1998 | Kon |
| 5,914,890 A | 6/1999 | Sarangapani et al. |
| 5,925,089 A | 7/1999 | Fujime |
| 5,950,147 A | 9/1999 | Sarangapani et al. |
| 5,966,312 A | 10/1999 | Chen |
| 5,987,976 A | 11/1999 | Sarangapani |
| 6,086,617 A | 7/2000 | Waldon et al. |
| 6,092,016 A | 7/2000 | Sarangapani et al. |
| 6,108,635 A * | 8/2000 | Herren et al. ............ 705/2 |
| 6,119,074 A | 9/2000 | Sarangapani |
| 6,145,066 A | 11/2000 | Atkin |
| 6,195,648 B1 | 2/2001 | Simon et al. |
| 6,199,007 B1 | 3/2001 | Zavarehi et al. |
| 6,208,982 B1 | 3/2001 | Allen, Jr. et al. |
| 6,223,133 B1 | 4/2001 | Brown |
| 6,236,908 B1 | 5/2001 | Cheng et al. |
| 6,240,343 B1 | 5/2001 | Sarangapani et al. |
| 6,267,722 B1 * | 7/2001 | Anderson et al. ............ 600/300 |
| 6,269,351 B1 | 7/2001 | Black |
| 6,298,718 B1 | 10/2001 | Wang |
| 6,370,544 B1 | 4/2002 | Krebs et al. |
| 6,394,952 B1 * | 5/2002 | Anderson et al. ............ 600/300 |
| 6,405,122 B1 | 6/2002 | Yamaguchi |
| 6,438,430 B1 | 8/2002 | Martin et al. |
| 6,442,511 B1 | 8/2002 | Sarangapani et al. |
| 6,477,660 B1 | 11/2002 | Sohner |
| 6,513,018 B1 | 1/2003 | Culhane |
| 6,546,379 B1 | 4/2003 | Hong et al. |
| 6,584,768 B1 | 7/2003 | Hecker et al. |
| 6,594,989 B1 | 7/2003 | Hepburn et al. |
| 6,698,203 B2 | 3/2004 | Wang |
| 6,711,676 B1 | 3/2004 | Zomaya et al. |
| 6,721,606 B1 | 4/2004 | Kaji et al. |
| 6,725,208 B1 | 4/2004 | Hartman et al. |
| 6,763,708 B2 | 7/2004 | Ting et al. |
| 6,775,647 B1 | 8/2004 | Evans et al. |
| 6,785,604 B2 | 8/2004 | Jacobson |
| 6,810,442 B1 | 10/2004 | Lin et al. |
| 6,823,675 B2 | 11/2004 | Brunell et al. |
| 6,859,770 B2 | 2/2005 | Ramsey |
| 6,859,785 B2 | 2/2005 | Case |
| 6,865,883 B2 | 3/2005 | Gomulka |
| 6,867,051 B1 * | 3/2005 | Anderson et al. ............ 436/518 |
| 6,882,929 B2 | 4/2005 | Liang et al. |
| 6,895,286 B2 | 5/2005 | Kaji et al. |
| 6,935,313 B2 | 8/2005 | Jacobson |
| 6,936,476 B1 * | 8/2005 | Anderson et al. ............ 436/518 |
| 6,941,287 B1 | 9/2005 | Vaidyanathan et al. |
| 6,952,662 B2 | 10/2005 | Wegerich et al. |
| 6,976,062 B1 | 12/2005 | Denby et al. |
| 7,000,229 B2 | 2/2006 | Gere |
| 7,024,343 B2 | 4/2006 | El-Ratal |
| 7,027,953 B2 | 4/2006 | Klein |
| 7,035,834 B2 | 4/2006 | Jacobson |
| 7,117,079 B2 | 10/2006 | Streichsbier et al. |
| 7,124,047 B2 | 10/2006 | Zhang et al. |
| 7,127,892 B2 | 10/2006 | Akins et al. |
| 7,174,284 B2 | 2/2007 | Dolansky et al. |
| 7,178,328 B2 | 2/2007 | Solbrig |
| 7,191,161 B1 | 3/2007 | Rai et al. |
| 7,194,392 B2 | 3/2007 | Tuken et al. |
| 7,213,007 B2 | 5/2007 | Grichnik |
| 7,270,970 B2 * | 9/2007 | Anderson et al. .......... 435/7.94 |
| 7,356,393 B1 | 4/2008 | Schlatre et al. |
| 7,369,925 B2 | 5/2008 | Morioka et al. |
| 7,379,885 B1 * | 5/2008 | Zakim ........................... 705/2 |
| 7,472,096 B2 * | 12/2008 | Burges et al. ................. 706/20 |
| 7,487,134 B2 * | 2/2009 | Grichnik et al. .............. 706/60 |
| 2002/0014294 A1 | 2/2002 | Okano et al. |
| 2002/0016701 A1 | 2/2002 | Duret et al. |
| 2002/0042784 A1 | 4/2002 | Kerven et al. |
| 2002/0049704 A1 | 4/2002 | Vanderveldt et al. |
| 2002/0103996 A1 | 8/2002 | LeVasseur et al. |
| 2002/0198821 A1 | 12/2002 | Munoz |
| 2003/0018503 A1 | 1/2003 | Shulman |
| 2003/0055607 A1 | 3/2003 | Wegerich et al. |
| 2003/0093250 A1 | 5/2003 | Goebel |
| 2003/0126053 A1 | 7/2003 | Boswell et al. |
| 2003/0126103 A1 | 7/2003 | Chen et al. |
| 2003/0130855 A1 | 7/2003 | Babu et al. |
| 2003/0167354 A1 | 9/2003 | Peppers et al. |
| 2003/0187567 A1 | 10/2003 | Sulatisky et al. |
| 2003/0187584 A1 | 10/2003 | Harris |
| 2003/0200296 A1 | 10/2003 | Lindsey |
| 2004/0030420 A1 | 2/2004 | Ulyanov et al. |
| 2004/0034857 A1 | 2/2004 | Mangino et al. |
| 2004/0059518 A1 | 3/2004 | Rothschild |
| 2004/0077966 A1 | 4/2004 | Yamaguchi et al. |
| 2004/0122702 A1 | 6/2004 | Sabol et al. |
| 2004/0122703 A1 | 6/2004 | Walker et al. |
| 2004/0128058 A1 | 7/2004 | Andres et al. |
| 2004/0135677 A1 | 7/2004 | Asam |
| 2004/0138995 A1 | 7/2004 | Hershkowitz et al. |
| 2004/0153227 A1 | 8/2004 | Hagiwara et al. |
| 2004/0230404 A1 | 11/2004 | Messmer et al. |
| 2004/0267818 A1 | 12/2004 | Hartenstine |
| 2005/0047661 A1 | 3/2005 | Maurer |
| 2005/0055176 A1 | 3/2005 | Clarke et al. |
| 2005/0091093 A1 | 4/2005 | Bhaskaran et al. |
| 2005/0209943 A1 | 9/2005 | Ballow et al. |
| 2005/0210337 A1 | 9/2005 | Chester et al. |
| 2005/0240539 A1 | 10/2005 | Olavson |
| 2005/0261791 A1 | 11/2005 | Chen et al. |
| 2005/0262031 A1 | 11/2005 | Saidi et al. |
| 2005/0278227 A1 | 12/2005 | Esary et al. |
| 2005/0278432 A1 | 12/2005 | Feinleib et al. |
| 2006/0010057 A1 | 1/2006 | Bradway et al. |
| 2006/0010142 A1 | 1/2006 | Kim et al. |
| 2006/0010157 A1 | 1/2006 | Dumitrascu et al. |
| 2006/0025897 A1 | 2/2006 | Shostak et al. |
| 2006/0026270 A1 | 2/2006 | Sadovsky et al. |
| 2006/0026587 A1 | 2/2006 | Lemarroy et al. |
| 2006/0064474 A1 | 3/2006 | Feinleib et al. |
| 2006/0068973 A1 | 3/2006 | Kappauf et al. |
| 2006/0129289 A1 | 6/2006 | Kumar et al. |
| 2006/0130052 A1 | 6/2006 | Allen et al. |
| 2006/0229753 A1 | 10/2006 | Seskin et al. |
| 2006/0229769 A1 | 10/2006 | Grichnik et al. |
| 2006/0229852 A1 | 10/2006 | Grichnik et al. |
| 2006/0229854 A1 | 10/2006 | Grichnik et al. |
| 2006/0230018 A1 | 10/2006 | Grichnik et al. |
| 2006/0230097 A1 | 10/2006 | Grichnik et al. |
| 2006/0230313 A1 | 10/2006 | Grichnik et al. |
| 2006/0241923 A1 | 10/2006 | Xu et al. |

| | | | |
|---|---|---|---|
| 2006/0247798 | A1 | 11/2006 | Subbu et al. |
| 2007/0061144 | A1 | 3/2007 | Grichnik et al. |
| 2007/0094048 | A1 | 4/2007 | Grichnik |
| 2007/0094181 | A1 | 4/2007 | Tayebnejad et al. |
| 2007/0118338 | A1 | 5/2007 | Grichnik et al. |
| 2007/0124237 | A1 | 5/2007 | Sundararajan et al. |
| 2007/0150332 | A1 | 6/2007 | Grichnik et al. |
| 2007/0168494 | A1 | 7/2007 | Liu et al. |
| 2007/0179769 | A1 | 8/2007 | Grichnik et al. |
| 2007/0203864 | A1 | 8/2007 | Grichnik |
| 2008/0154811 | A1 | 6/2008 | Grichnik et al. |

FOREIGN PATENT DOCUMENTS

| | | |
|---|---|---|
| EP | 1367248 | 12/2003 |
| EP | 1418481 | 5/2004 |
| JP | 10-332621 | 12/1998 |
| JP | 11-351045 | 12/1999 |
| JP | 2002-276344 | 9/2002 |
| WO | WO97/42581 | 11/1997 |
| WO | WO02/057856 | 7/2002 |
| WO | WO2006/017453 | 2/2006 |

OTHER PUBLICATIONS

Mining Risk Information in Hospital Information Systems as Risk Mining Tsumoto, S.; Yokoyama, S.; Matsuoka, K.; Complex Medical Engineering, 2007. CME 2007. IEEE/ICME International Conference on May 23-27, 2007 pp. 1917-1921 Digital Object Identifier 10.1109/ICCME.2007.4382082.*

Using upper bounds on attainable discrimination to select discrete valued features Lovell, D.R.; Dance, C.R.; Niranjan, M.; Prager, R.W.; Dalton, K.J.; Neural Networks for Signal Processing [1996] VI. Proceedings of the 1996 IEEE Signal Processing Society Workshop Sep. 4-6, 1996 pp. 233-242 Digital Object Identifier 10.1109/NNSP.1996.548353.*

Aerospace robotics in supermaneuverable flight: defining the set of attainable motion fields in existing aircraft and motion simulators Repperger, D.W.; Roberts, R.G.; Aerospace and Electronics Conference, 1993. NAECON 1993., Proceedings of the IEEE 1993 National May 24-28, 1993 pp. 679-685 vol. 2 Digital Object Identifier 10.1109/NAECON.1993.*

Pending U.S. Appl. No. 11/257,341, filed Oct. 25, 2005, titled "Medical Risk Stratifying Method and System," to Anthony Grichnik et al.

Allen et al., "Supersaturated Designs That Maximize the Probability of Identifying Active Factors," 2003 American Statistical Association and the American Society for Quality, Technometrics, vol. 45, No. 1, Feb. 2003, pp. 1-8.

April, Jay et al., "Practical Introduction to Simulation Optimization," Proceedings of the 2003 Winter Simulation Conference, pp. 71-78.

Bandte et al., "Viable Designs Through a Joint Probabilistic Estimation Technique," SAE International, and the American Institute of Aeronautics and Astronautics, Inc., Paper No. 1999-01-5623, 1999, pp. 1-11.

Beisl et al., "Use of Genetic Algorithm to Identify the Source Point of Seepage Slick Clusters Interpreted from Radarsat-1 Images in the Gulf of Mexico," Geoscience and Remote Sensing Symposium, 2004, Proceedings, 2004 IEEE International Anchorage, AK, Sep. 20-24, 2004, vol. 6, Sep. 20, 2004, pp. 4139-4142.

Berke et al., "Optimum Design of Aerospace Structural Components Using Neural Networks," Computers and Structures, vol. 48, No. 6, Sep. 17, 1993, pp. 1001-1010.

Bezdek, "Genetic Algorithm Guided Clustering," IEEE 0-7803-1899-4/94, 1994, pp. 34-39.

Brahma et al., "Optimization of Diesel Engine Operating Parameters Using Neural Networks," SAE Technical Paper Series, 2003-01-3228, Oct. 27-30, 2003 (11 pages).

Chau et al., "Use of runs test to access cardiovascular autonomic function in diabetic subjects," Abstract, Diabetes Care, vol. 17, Issue 2, pp. 146-148, available at http://care.diabetesjournals.org/cgi/content/abstract/17/2/146).

Chung et al., "Process Optimal Design in Forging by Genetic Algorithm," Journal of Manufacturing Science and Engineering, vol. 124, May 2002, pp. 397-408.

Cox et al., "Statistical Modeling for Efficient Parametric Yield Estimation of MOS VLSI Circuits," IEEE, 1983, pp. 242-245.

De Maesschalck et al., "The Mahalanobis Distance," Chemometrics and Intelligent Laboratory Systems, vol. 50, No. 1, Jan. 2000, pp. 1-18.

Dikmen et al., "Estimating Distributions in Genetic Algorithms," ISCIS 2003, LNCS 2869, 2003, pp. 521-528.

Galperin, G., et al., "Parallel Monte-Carlo Simulation of Neural Network Controllers," available at http://www-fp.mcs.anl.gov/ccst/research/reports_pre1998/neural_network/galperin.html, printed Mar. 11, 2005 (6 pages).

Gletsos et al., "A Computer-Aided Diagnostic System to Characterize CT Focal Liver Lesions: Design and Optimization of a Neural Network Classifier," IEEE Transactions on Information Technology in Biomedicine, vol. 7, No. 3, Sep. 2003 pp. 153-162.

Grichnik et al., "An Improved Metric for Robust Engineering," Proceedings of the 2007 International Conference on Scientific Computing, Las Vegas, NV (4 pages).

Grichnik et al., Copending U.S. Appl. No. 11/529,267, filed Sep. 29, 2006, entitled Virtual Sensor Based Engine Control System and Method.

Grichnik et al., Copending U.S. Appl. No. 11/730,363, filed Mar. 30, 2007, entitled Prediction Based Engine Control System and Method.

Grichnik et al., Copending U.S. Appl. No. 11/812,164, filed Jun. 15, 2007, entitled Virtual Sensor System and Method.

Grichnik et al., Copending U.S. Appl. No. 11/979,408, filed Nov. 2, 2007, entitled Virtual Sensor Network (VSN) System and Method.

Holland, John H., "Genetic Algorithms," Scientific American, Jul. 1992, pp. 66-72.

Hughes et al., "Linear Statistics for Zeros of Riemann's Zeta Function," C.R. Acad. Sci. Paris, Ser. I335 (2002), pp. 667-670.

Ko et al., "Application of Artificial Neural Network and Taguchi Method to Perform Design in Metal Forming Considering Workability," International Journal of Machine Tools & Manufacture, vol. 39, No. 5, May 1999, pp. 771-785.

Kroha et al., "Object Server on a Parallel Computer," 1997 IEEE 0-8186-8147-0/97, pp. 284-288.

Mavris et al., "A Probabilistic Approach to Multivariate Constrained Robust Design Simulation," Society of Automotive Engineers, Inc., Paper No. 975508, 1997, pp. 1-11.

National Institute of Health, "10-year CVD Risk Calculator" available at http://hin.nhlbi.nih.gov/atpiii/calculator.asp?usertype=prof, printed Aug. 2, 2005, 2 pages.

Obayashi et al, "Multiobjective Evolutionary Computation for Supersonic Wing-Shape Optimization," IEEE Transactions on Evolutionary Computation, vol. 4, No. 2, Jul. 2000, pp. 182-187.

Simpson et al., "Metamodels for Computer-Based Engineering Design: Survey & Recommendations," Engineering with Computers, 2001, vol. 17, pp. 129-150.

Song et al., "The Hyperellipsoidal Clustering Using Genetic Algorithm," 1997 IEEE International Conference on Intelligent Processing Systems, Oct. 28-31, 1997, Beijing, China, pp. 592-596.

Sytsma, Sid, "Quality and Statistical Process Control," available at http://www.sytsma.com/tqmtools/ctlchtprinciples.html, printed Apr. 7, 2005, 6 pages.

Taguchi et al., "The Mahalanobis-Taguchi Strategy," A Pattern Technology System, John Wiley & Sons, Inc., 2002, 234 pages.

Taylor et al., "Guidelines for Evaluating and Expressing the Uncertainty of NIST Measurement Results," NIST Technical Note 1297, 1994 Edition, United States Dept. of Commerce, National Institute of Standards and Technology (25 pages).

Thompson, G.J. et al., "Neural Network Modelling of the Emissions and Performance of a Heavy-Duty Diesel Engine," Proc. Instu. Mech. Engrs., vol. 214, Part D (2000), pp. 111-126.

Traver, Michael L. et al., "A Neural Network-Based Virtual NOx Sensor for Diesel Engines," West Virginia University, Mechanical and Aerospace Engineering Dept., Morgantown, WV 26506-6101, 6106, 7 pages.

Traver, Michael L. et al., "Neural Network-Based Diesel Engine Emissions Prediction Using In-Cylinder Combustion Pressure," International Spring Fuels & Lubricants Meeting & Exposition, SAE Technical Paper Series, May 3-6, 1999, 17 pages.

Woodall, Tsui et al., "A Review and Analysis of the Mahalanobis-Taguchi System," Technometrics, Feb. 2003, vol. 45, No. 1 (15 pages).

Wu et al., "Cam-phasing Optimization Using Artificial Neural Networks as Surrogate Models—Fuel Consumption and Nox Emissions," SAE Technical Paper Series, 2006-01-1512, Apr. 3-6, 2006 (19 pages).

Yang et al., "Similar Cases Retrieval from the Database of Laboratory Test Results," Journal of Medical Systems, vol. 27, No. 3, Jun. 2003, pp. 271-282.

Yuan et al., "Evolutionary Fuzzy C-Means Clustering Algorithm," 1995 IEEE 0-7803-2461-7/95, pp. 2221-2226.

* cited by examiner

EXPERT KNOWLEDGE COMBINATION PROCESS BASED MEDICAL RISK STRATIFYING METHOD AND SYSTEM

CROSS REFERENCE TO RELATED APPLICATIONS

This application is a continuation-in-part application of U.S. patent application Ser. No. 11/257,341, filed on Oct. 25, 2005, now U.S. Pat. No. 7,487,134 the benefit of priority from which is herein claimed.

TECHNICAL FIELD

This disclosure relates generally to computer based process modeling techniques and, more particularly, to methods and systems for stratifying medical risk using process models based on an expert knowledge combination process.

BACKGROUND

Medical-related information comes from many different sources, such as clinical data or non-clinical data. Medical-related information may be used by health care professionals for the prescription and analysis of tests and/or for the diagnosis and treatment of medical events. Medical-related information may also be used to analyze medical risks. Medical risk analysis may be an important tool to analyze the possibility of a certain type of medical risk based on certain types of medical-related information. For example, medical risk analysis may be used to analyze the possibility of lung disease based on whether or not a person is a smoker.

Process models and algorithms may be used to perform medical risk analysis. For example, U.S. Patent Application Publication No. 20040122703 to Walker et al. discloses a technique for developing a model of medical conditions and situations from medical data by using database techniques and neural network methods. However, such conventional techniques often fail to address inter-correlation between individual medical records, especially at the time of generation and/or optimization of process models, used for correlating medical information to medical risks. Furthermore, such conventional techniques often fail to address other issues such as multiple medical risks models and conflict medical records from the multiple models.

Methods and systems consistent with certain features of the disclosed systems are directed to solving one or more of the problems set forth above.

SUMMARY OF THE INVENTION

One aspect of the present disclosure includes a method for a medical risk stratification system. The method may include obtaining data records associated with one or more health variables and a plurality of medical risks from a plurality of MRS models based on an expert knowledge combination process and establishing a medical risk process model indicative of interrelationships between the plurality of medical risks and a plurality of health parameters based on the data records. The method may also include obtaining a set of values corresponding to the plurality of health parameters and calculating values of the plurality of medical risks simultaneously based upon the set of values corresponding to the plurality of health parameters and the medical risk process model. Further, the method may include optimizing the plurality of health parameters to minimize the plurality of medical risks simultaneously and presenting the values of the plurality of medical risks.

Another aspect of the present disclosure includes a computer system. The computer may include a database and a processor. The database may include data records associating a plurality of medical risks and a plurality of health parameters. The processor may be configured to obtain data records associated with one or more health variables and a plurality of medical risks from a plurality of MRS models based on an expert knowledge combination process and to establish a medical risk process model indicative of interrelationships between the plurality of medical risks and a plurality of health parameters based on the data records. The processor may also be configured to obtain a set of values corresponding to the plurality of health parameters and to calculate values of the plurality of medical risks simultaneously based upon the set of values corresponding to the plurality of health parameters and the medical risk process model. Further, the processor may be configured to optimize the plurality of health parameters to minimize the plurality of medical risks simultaneously and to present the values of the plurality of medical risks.

Another aspect of the present disclosure includes a computer-readable medium for use on a computer system configured to perform a medical risk stratification procedure. The computer-readable medium may have computer-executable instructions for performing a method. The method may include obtaining data records associated with one or more health variables and a plurality of medical risks from a plurality of MRS models based on an expert knowledge combination process and establishing a medical risk process model indicative of interrelationships between the plurality of medical risks and a plurality of health parameters based on the data records. The method may also include obtaining a set of values corresponding to the plurality of health parameters and calculating values of the plurality of medical risks simultaneously based upon the set of values corresponding to the plurality of health parameters and the medical risk process model. Further, the method may include optimizing the plurality of health parameters to minimize the plurality of medical risks simultaneously and presenting the values of the plurality of medical risks.

DETAILED DESCRIPTION

Reference will now be made in detail to exemplary embodiments, which are illustrated in the accompanying drawings. Wherever possible, the same reference numbers will be used throughout the drawings to refer to the same or like parts.

Figure 1:
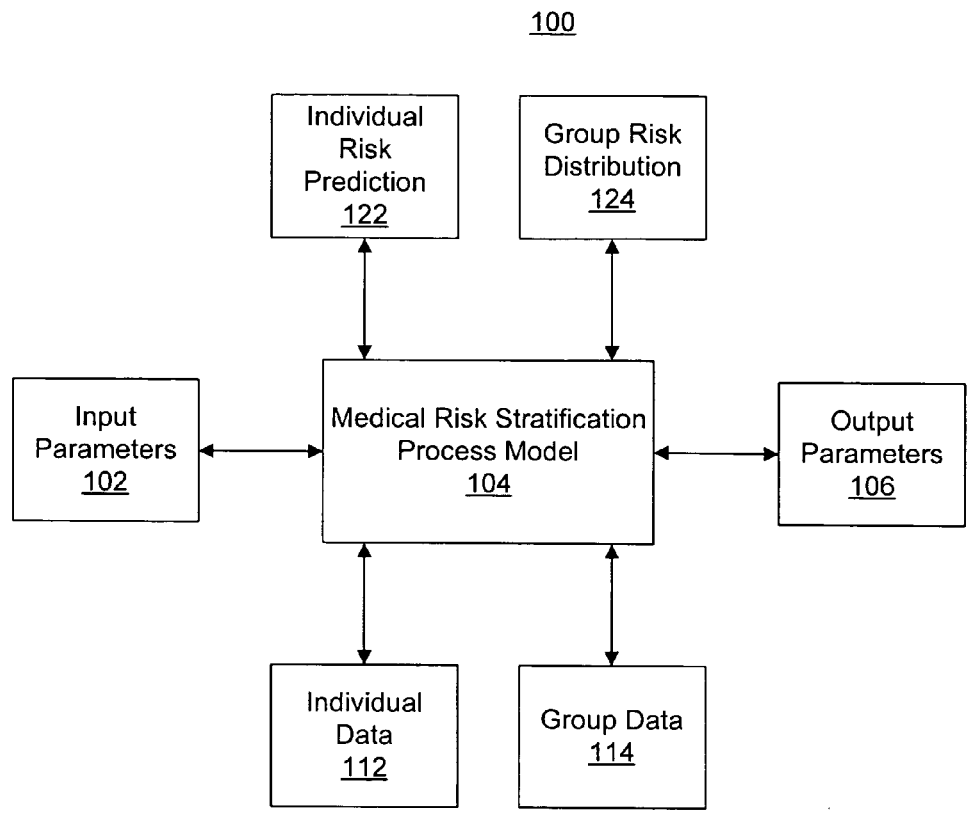
FIG. 1 is a pictorial illustration of an exemplary medical risk stratification process environment consistent with certain disclosed embodiments.

FIG. 1 illustrates a flowchart diagram of an exemplary medical risk stratification process modeling environment 100. As shown in FIG. 1, a medical risk stratification (MRS) process model 104 may be established to build interrelationships between input parameters 102 and output parameters 106. After MRS process model 104 is established, values of input parameters 102 may be provided to MRS process model 104 to predict values of output parameters 106 based on the given values of input parameters 102 and the interrelationships.

Input parameters 102 may include any appropriate type of data associated with a medical application. For example, input parameters 102 may include medical records from hospitals or other health institutions. Output parameters 106, on the other hand, may correspond to certain medical risks or any other types of output parameters used by the particular medical application.

MRS process model 104 may include any appropriate type of mathematical or physical model indicating interrelationships between input parameters 102 and output parameters 106. For example, MRS process model 104 may be a neural network based mathematical model that is trained to capture interrelationships between input parameters 102 and output parameters 106. Other types of mathematic models, such as fuzzy logic models, linear system models, and/or non-linear system models, etc., may also be used. MRS process model 104 may be trained and validated using data records collected from a particular application for which MRS process model 104 is established. That is, MRS process model 104 may be established according to particular rules corresponding to a particular type of model using the data records, and the interrelationships of MRS process model 104 may be verified by using part of the data records.

After MRS process model 104 is trained and validated, MRS process model 104 may be optimized to define a desired input space of input parameters 102 and/or a desired distribution of output parameters 106. The validated or optimized MRS process model 104 may used to produce corresponding values of output parameters 106 when provided with a set of values of input parameters 102. For example, MRS process model 104 may be used to produce individual risk prediction 122 based on individual data 112. Further, MRS process model 104 may also be used to find group risk prediction 124 based on group data 114.

Figure 2:
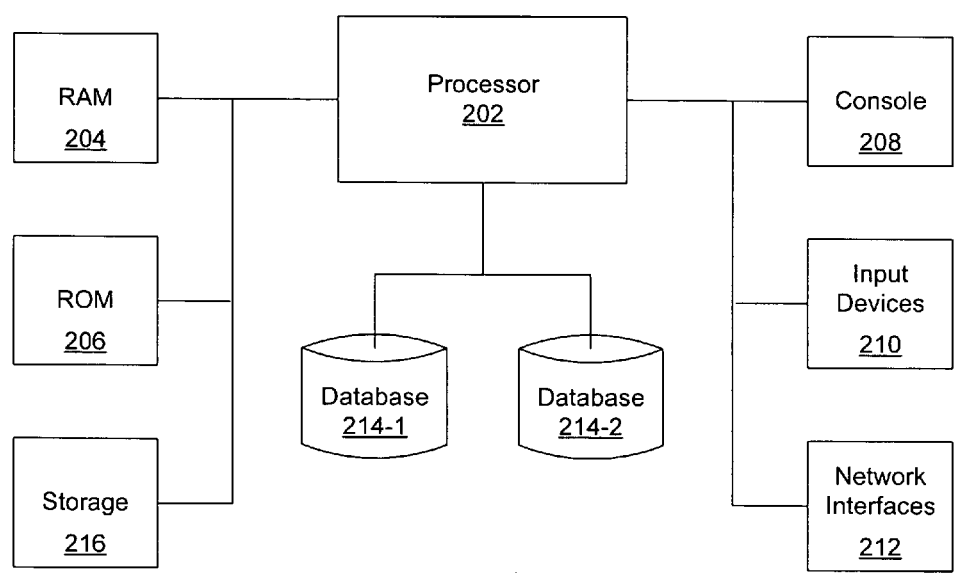
FIG. 2 illustrates a block diagram of a computer system consistent with certain disclosed embodiments.

The establishment and operations of MRS process model 104 may be carried out by one or more computer systems. FIG. 2 shows a functional block diagram of an exemplary computer system 200 that may be used to perform these modeling processes and operations.

As shown in FIG. 2, computer system 200 may include a processor 202, a random access memory (RAM) 204, a read-only memory (ROM) 206, a console 208, input devices 210, network interfaces 212, databases 214-1 and 214-2, and a storage 216. It is understood that the type and number of listed devices are exemplary only and not intended to be limiting. The number of listed devices may be changed and other devices may be added.

Processor 202 may include any appropriate type of general purpose microprocessor, digital signal processor, or microcontroller. Processor 202 may execute sequences of computer program instructions to perform various processes as explained above. The computer program instructions may be loaded into RAM 204 for execution by processor 202 from a read-only memory (ROM), or from storage 216. Storage 216 may include any appropriate type of mass storage provided to store any type of information that processor 202 may need to perform the processes. For example, storage 216 may include one or more hard disk devices, optical disk devices, or other storage devices to provide storage space.

Console 208 may provide a graphic user interface (GUI) to display information to users of computer system 200. Console 208 may include any appropriate type of computer display device or computer monitor. Input devices 210 may be provided for users to input information into computer system 200. Input devices 210 may include a keyboard, a mouse, or other optical or wireless computer input devices, etc. Further, network interfaces 212 may provide communication connections such that computer system 200 may be accessed remotely through computer networks via various communication protocols, such as transmission control protocol/internet protocol (TCP/IP), hyper text transfer protocol (HTTP), etc.

Databases 214-1 and 214-2 may contain model data and/or any information related to data records under analysis, such as training and testing data. Databases 214-1 and 214-2 may include any type of commercial or customized databases. Databases 214-1 and 214-2 may also include analysis tools for analyzing the information in the databases. Processor 202 may also use databases 214-1 and 214-2 to determine and store performance characteristics of MRS process model 104.

Figure 3:
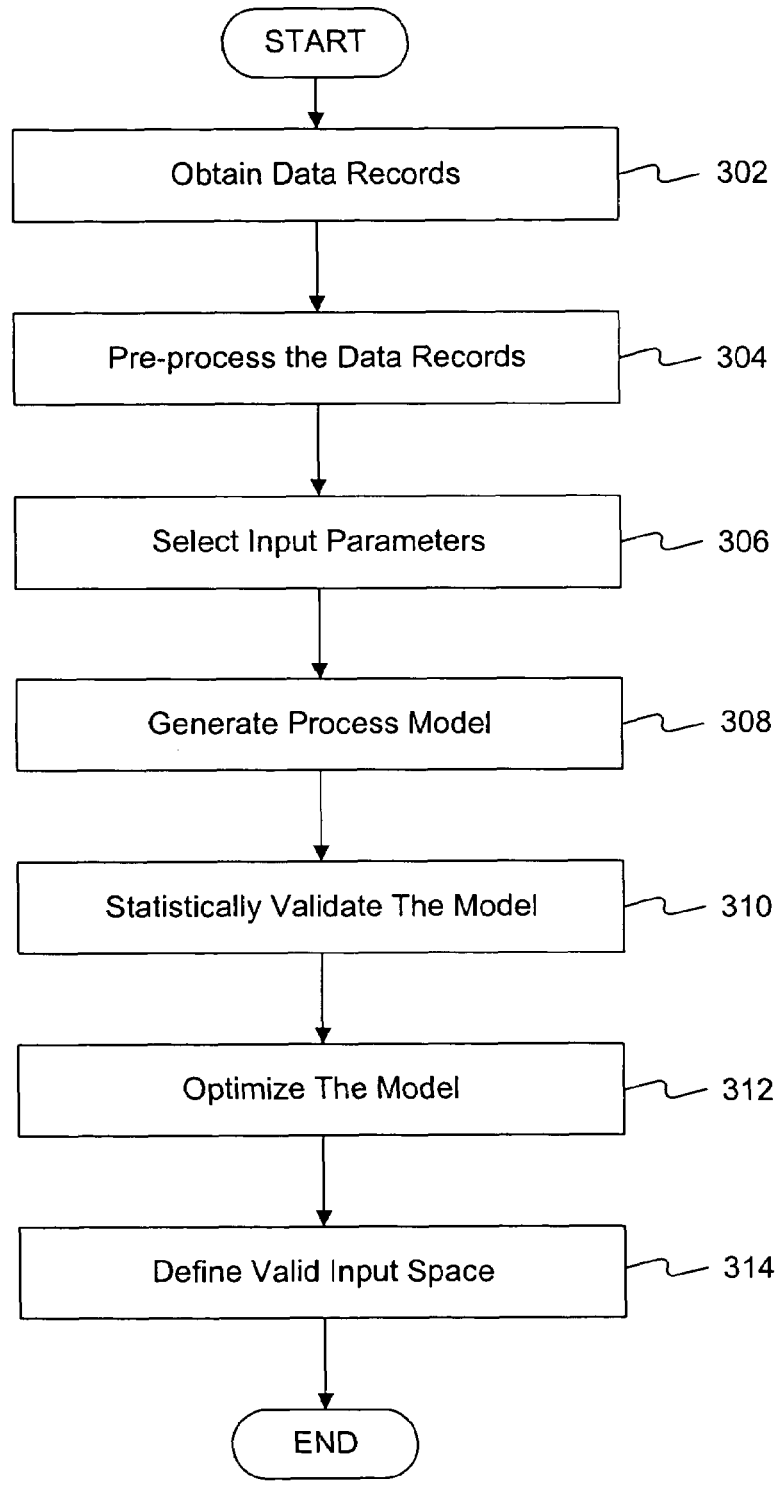
FIG. 3 illustrates a flowchart of an exemplary medical risk stratification model generation and optimization process consistent with certain disclosed embodiments.

Processor 202 may perform a medical risk stratification model generation and optimization process to generate and optimize MRS process model 104. FIG. 3 shows an exemplary model generation and optimization process performed by processor 202.

As shown in FIG. 3, at the beginning of the model generation and optimization process, processor 202 may obtain data records associated with input parameters 102 and output parameters 106 (step 302). The data records may include information characterizing individuals or a population, genetic information, medical events and states, treatments, diagnosis, and prognosis characterizations, etc. In particular, the data records may include demographic data (e.g., age, race, sex, work place, residence, life style, etc.), self-reported data (e.g., surveys captured intermittently from individuals or members of a population), prescription drug information (e.g., types and/or amount of prescription drugs taken by an individual or a population), diagnostic records (e.g., clinical tests and results), and treatment data (e.g., illness, treatment, hospital, and/or doctor, etc.).

For example, the data records may include information about parameters related to an individual patient's blood, urine, saliva and other fluid analysis (e.g., gastrointestinal, reproductive, and cerebrospinal fluid analysis). The data records may also include data obtained from various medical analysis systems, such as polymerase (PCR) chain reaction analysis systems, genetic marker analysis systems, radioimmunoassay systems, chromatography analysis systems, and/or receptor assay systems, etc. Data from other analysis systems, such as tissue analysis systems, cytology and tissue typing systems, and immunocytochemistry and histopathological analysis systems may also be included.

Further, the data records may include clinically measured information of individual patients, such as clinical medical data (e.g., age, sex, height, exercise level, cholesterol level, blood pressure, diet, particular diseases and treatments, health habit, etc.) or other clinical test data such as electroencephalographs (EEG), electrocardiographs (ECG), electromyographs (EMG), electrical impedance tomographs (EIT), nerve conduction test data, electronystagmographs (ENG), X-ray images, magnetic resonance (MR) images, computed tomography (CT) images, positron emission tomographs (PET), and/or flouorography, mammography, sonography, infrared, nuclear, and thermoacoustic images, etc.

The data records may also be collected from experiments designed for collecting such data. Alternatively, the data records may be generated artificially by other related processes, such as other medical modeling or analysis processes. The data records may also include training data used to build MRS process model 104 and testing data used to validate MRS process model 104. In addition, the data records may also include simulation data used to observe and optimize MRS process model 104.

As used herein, when data records are used to build MRS process model 104, the information contained in the data records, such as characteristic data, demographic data, self-reported data, prescription drug information, diagnostic records, and treatment data, etc, may be referred to as health variables or variables. For example, one variable may be an age of a person; another variable may be blood pressure of the person; yet another variable may be an exercise level of the person, etc. Any measurable parameter, either directly or indirectly, may be used as a variable for MRS process model 104 or other MRS models to predict a particular medical risk or risks.

In certain embodiments, processor 202 may also create data records using other MRS systems or MRS models, such as publicly available MRS models from Harvard School of Public Health, the American Diabetes Association, the American Heart Association, and the National Institute of Health, etc. Processor 202 may also use data records from the other MRS systems or MRS models. These individual MRS models may calculate certain medical risks based on relationships between certain variables and a particular medical risk, such as diabetes, cardiovascular disease (CVD), etc. These individual MRS models may be well established based on a particular medical theory or a particular data collection method. Each individual MRS model may be referred to as an expert knowledge base.

Figure 8:
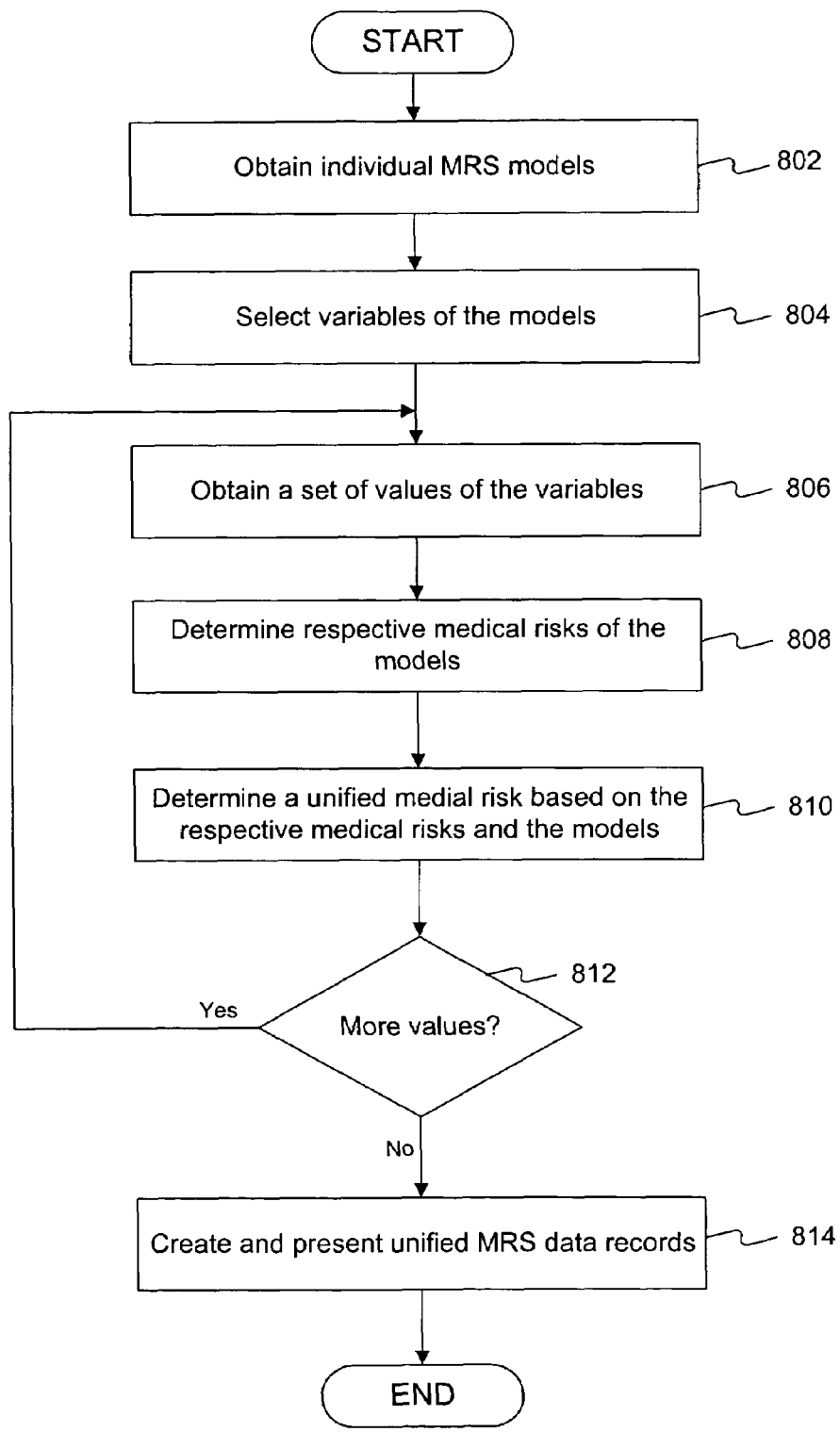
FIG. 8 shows an exemplary expert knowledge combination process consistent with certain disclosed embodiments.

Processor 202 may create data records based on any individual expert knowledge base for creating MRS process model 104. In certain embodiments, processor 202 may use multiple expert knowledge bases to create MRS process model 104. However, when multiple expert bases are used, medical risks or risk stratifications made by the multiple expert knowledge bases may be different from, inconsistent with, or even conflicting with each other. For example, a same person with a set of characteristics (e.g., a set of particular values of certain variables) may have different stratifications under different expert knowledge bases. It may then be difficult to choose a particular expert knowledge base as a more correct model or to reconcile different expert knowledge bases. Processor 202 may perform an expert knowledge combination process to combine the medical risks or risk stratifications of multiple expert knowledge bases to generate suitable data records used for MRS process model 104. FIG. 8 shows an exemplary expert knowledge combination process performed by processor 202.

As shown in FIG. 8, at the beginning of the expert knowledge combination process, processor 202 may obtain individual MRS models, or individual expert knowledge bases, from multiple MRS models (step 802). Processor 202 may obtain data records to be used as inputs to the multiple MRS models, and/or may also obtain data records associated with the multiple MRS models. Further, processor 202 may analyze each individual MRS model to determine what variables are required to be included in the data records by each individual MRS model. As explained above, the variables may include information such as personal characteristic data, demographic data, clinic data, medical history data, etc.

Different MRS models may include different variables. For example, two cardiovascular disease MRS models may adopt different variables about characteristics of a person under analysis. The first MRS model may include variables such as age, gender, cholesterol level, blood pressure, smoker, high blood pressure medicine, etc.; and the second MRS model may include gender, age, cvd history, weight, height, high blood pressure, high blood sugar, cholesterol level, diet, smoker, exercise level, etc. Among these variables, age, gender, cholesterol level, blood pressure, and smoker exist in both the first and the second MRS models.

After determining variables required by the individual MRS models, processor 202 may select variables of the MRS models (step 804). The variables selected may include a combination of variables required by each individual MRS model and may be referred to as model variables of the multiple MRS models. The variables may include common variables that are required by all of the multiple MRS models. On the other hand, the variables may also include uncommon variables that are not required by all of the multiple MRS models. Therefore, the variable may be a super set of variables combining most or all required variables of the multiple MRS models.

In the example above, processor 202 may select age, gender, cholesterol level, blood pressure, smoker, high blood pressure medicine, cvd history, weight, height, high blood sugar, diet, exercise level, etc., as the variables. Among the selected variables, age, gender, cholesterol level, blood pressure, and smoker may be treated as the common variables for the first and the second MRS models, and high blood pressure medicine, cvd history, weight, height, high blood sugar, diet, exercise level may be treated as uncommon variables for the first and the second MRS models.

Processor 202 may obtain a set of values for the variables (step 806). The set of values of the variables may be referred to as an instance of the variables (a data record) with each variable having a particular value. As explained above, the set of values of the variables may indicate certain characteristics or attributes of the person under analysis. Thus, this set of values of the variables may be inputted to the multiple MRS models and the multiple MRS models may generate medical risks or risk stratifications that reflect medical risks of the same person under different MRS models.

For example, in the cardiovascular disease example above, a person under analysis may be represented by a particular set of values, e.g., 30 years of age, male, 120 cholesterol level, 110/80 blood pressure, non-smoker, of the variables of age, gender, cholesterol level, blood pressure, and smoker. Therefore, a data record having the particular set of values may be inputted to the first MRS model and the second MRS model and may represent the same person having different cardiovascular disease risks under the first and the second MRS models.

Processor 202 may obtain the set of values for the variables from any appropriate sources, such as database 214-1 or 214-2. Processor 202 may randomly or sequentially obtain a data record from an MRS model and may perform certain search algorithms to select data records with the same set of values of the common variables in other remaining MRS models. Processor 202 may also combine data records from the individual MRS models to obtain the set of values for the variables.

Further, processor 202 may determine respective medical risks (e.g., cardiovascular disease risk, etc.) based on the individual MRS models (step 808). Processor 202 may input the data record with the set of values of the variables to the corresponding MRS model and may derive a respective medical risk from the corresponding MRS model. After all the respective medical risks are determined, processor 202 may determine a unified medical risk of all respective medical risks corresponding to the set of values of variables (step 810).

Processor 202 may determine the unified medical risk by combining the respective medical risks from the individual MRS models. In certain embodiments, processor 202 may perform the combination based on the concept of the Euclidean (geometric) distance. For example, each MRS model may be represented by an axis or a dimension in an Euclidean space. A particular axis may represent a particular medical risk that a particular MRS model generates. Therefore, multiple MRS models may create multiple axes or multiple dimensions in the Euclidean space with each axis representing the particular medical risk generated by each particular MRS model. Processor 202 may then determine the unified medical risk as a point in the multiple-dimension Euclidean space, whose position may be determined by the respective coordinates, i.e., values of the respective medical risks, of the multiple axes or dimensions. Processor 202 may determine the value of the unified medical risk as the distance between the origin (0) and the multiple-dimension point.

For the cardiovascular disease example above, where only two dimensions or axes are involved, the first MRS model may represent an x-axis and the second MRS model may represent a y-axis. For a set of values of variables (e.g., age, gender, cholesterol level, blood pressure, and smoker, etc.), if the first MRS model has a corresponding medical risk $x_1$ and the second MRS model has a corresponding medical risk $y_1$, the unified medical risk may be represented by a two-dimensional point $(x_1, y_1)$ with the value of $(x_1^2 + y_1^2)^{1/2}$, the distance from the origin $(0, 0)$ and $(x_1, y_1)$.

Similarly, for an m-dimensional space (e.g., with m MRS models), where m is an integer representing the total number of MRS models, the unified medical risk may be represented by an m-dimensional point $(x_1, x_2, x_3, \ldots, x_m)$, where $x_m$, (m=1, 2, ..., m) represents m coordinates, individual medical risks of corresponding MRS models. The value of the unified medical risk may then be $(x_1^2 + x_2^2 + + x_m^2)^{1/2}$. Although only 2-norm distance is used in the examples above, other norms may also be used. Further, other types of distances, such as arithmetic mean, geometric mean, logarithmic scaling, Mahalanobis distance, etc., may also be used to combine the individual medical risks.

Although only one medical risk (e.g., cardiovascular disease) is illustrated, a plurality of types of medical risks may be included with each type medical risk having a unified medical risk calculated separately according to the above descriptions. For example, processor 202 may select common medical risks among the multiple MRS models and process the common medical risks one by one.

After determining the unified medical risk (step 810), processor 202 may include the unified medical risk in the data records containing the variables of the multiple MRS models. Processor 202 may further determine whether more values or more data records need to be analyzed (step 812). If processor 202 determines that more data records need to be analyzed (step 812; yes), processor 202 may continue the expert knowledge combination process from step 806. On the other hand, if processor 202 determines that no more data record needs to be analyzed, processor 202 may proceed to create and present unified MRS data records (step 814).

Processor 202 may combine data records from the multiple MRS models or expert knowledge bases using the unified medical risks. For example, processor 202 may select data records including unified medical risks from the multiple MRS models and create a new database containing all the selected data records. The select data records including unified medical risks from the multiple MRS models may also be referred to as a composite MRS model. In one embodiment, the multiple MRS models may include one or more MRS process model 104. Optionally, processor 202 may also present the unified data records to a user of computer system 202 via, for example, console 208, or present the unified data records to other application programs or systems. Further, data records of multiple medical risks generated by the multiple MRS models may also be created according to the principle described above.

Returning to FIG. 3, once the data records are obtained (step 302), processor 202 may pre-process the data records to clean up the data records for obvious errors and to eliminate redundancies (step 304). The data records may reflect characteristics of input parameters 102 and output parameters 106, such as statistic distributions, normal ranges, and/or precision tolerances, etc. Processor 202 may remove approximately identical data records and/or remove data records that are out of a reasonable range in order to be meaningful for model generation and optimization. After the data records have been pre-processed, processor 202 may select proper input parameters by analyzing the data records (step 306).

The data records may be associated with many input variables, such as variables corresponding to demographic data, self-reported data, prescription drug information, diagnostic records, and treatment data, etc. The number of input variables may be greater than the number of input parameters 102 used for MRS process model 104, that is, input parameters 102 may be a subset of the input variables. For example, the data records may be associated with several medical conditions, such as lung, liver, heart, and/or other organs; while input parameters 102 of a particular process, such as CVD, may only include heart related information and/or information on blood pressure, cholesterol level, and/or lifestyle, etc.

In certain situations, the number of input variables in the data records may exceed the number of the data records and lead to sparse data scenarios. Some of the extra input variables may have to be omitted in certain mathematical models. The number of the input variables may need to be reduced to create mathematical models within practical computational time limits.

Processor 202 may select input parameters 102 according to predetermined criteria. For example, processor 202 may choose input parameters 102 by experimentation and/or expert opinions. Alternatively, in certain embodiments, processor 202 may select input parameters based on a mahalanobis distance between a normal data set and an abnormal data set of the data records. The normal data set and abnormal data set may be defined by processor 202 using any appropriate method. For example, the normal data set may include characteristic data associated with input parameters 102 that produce desired output parameters. On the other hand, the abnormal data set may include any characteristic data that may be out of tolerance or may need to be avoided. The normal data set and abnormal data set may be predefined by processor 202.

Mahalanobis distance may refer to a mathematical representation that may be used to measure data profiles based on correlations between parameters in a data set. Mahalanobis distance differs from Euclidean distance in that mahalanobis distance takes into account the correlations of the data set. Mahalanobis distance of a data set X (e.g., a multivariate vector) may be represented as $$MD_i = (X_i - \mu_x)\Sigma^{-1}(X_i - \mu_x)' \quad (1)$$

where $\mu_x$ is the mean of X and $\Sigma^{-1}$ is an inverse variance-covariance matrix of X. $MD_i$ weights the distance of a data point $X_i$ from its mean $\mu_x$ such that observations that are on the same multivariate normal density contour will have the same distance. Such observations may be used to identify and select correlated parameters from separate data groups having different variances.

Processor 202 may select a desired subset of input parameters such that the mahalanobis distance between the normal data set and the abnormal data set is maximized or optimized. A genetic algorithm may be used by processor 202 to search input parameters 102 for the desired subset with the purpose of maximizing the mahalanobis distance. Processor 202 may select a candidate subset of input parameters 102 based on a predetermined criteria and calculate a mahalanobis distance $MD_{normal}$ of the normal data set and a mahalanobis distance $MD_{abnormal}$ of the abnormal data set. Processor 202 may also calculate the mahalanobis distance between the normal data set and the abnormal data (i.e., the deviation of the mahalanobis distance $MD_x = MD_{normal} - MD_{abnormal}$). Other types of deviations, however, may also be used.

Processor 202 may select the candidate subset of input variables 102 if the genetic algorithm converges (i.e., the genetic algorithm finds the maximized or optimized mahalanobis distance between the normal data set and the abnormal data set corresponding to the candidate subset). If the genetic algorithm does not converge, a different candidate subset of input variables may be created for further searching. This searching process may continue until the genetic algorithm converges and a desired subset of input variables (e.g., input parameters 102) is selected.

After selecting input parameters 102 (e.g., age, sex, height, exercise level, cholesterol level, blood pressure, diet, particular diseases and treatments, health habit, etc.), processor 202 may generate MRS process model 104 to build interrelationships between input parameters 102 and output parameters 106 (step 308). In certain embodiments, MRS process model 104 may correspond to a computational model, such as, for example, a computational model built on any appropriate type of neural network. The type of neural network computational model that may be used may include back propagation, feed forward models, cascaded neural networks, and/or hybrid neural networks, etc. Particular types or structures of the neural network used may depend on particular applications. Other types of computational models, such as linear system or non-linear system models, etc., may also be used.

The neural network computational model (i.e., MRS process model 104) may be trained by using selected data records. For example, the neural network computational model may include a relationship between output parameters 106 (e.g., medical risks, etc.) and input parameters 102 (e.g., age, sex, weight, height, exercise level, cholesterol level, blood pressure, diet, habit, etc.). The neural network computational model may be evaluated by predetermined criteria to determine whether the training is completed. The criteria may include desired ranges of accuracy, time, and/or number of training iterations, etc.

After the neural network has been trained (i.e., the computational model has initially been established based on the predetermined criteria), processor 202 may statistically validate the computational model (step 310). Statistical validation may refer to an analyzing process to compare outputs of the neural network computational model with actual or expected outputs to determine the accuracy of the computational model. Part of the data records may be reserved for use in the validation process.

Alternatively, processor 202 may also generate simulation or validation data for use in the validation process. This may be performed either independently of a validation sample or in conjunction with the sample. Statistical distributions of inputs may be determined from the data records used for modeling. A statistical simulation, such as Latin Hypercube simulation, may be used to generate hypothetical input data records. These input data records are processed by the computational model, resulting in one or more distributions of output characteristics. The distributions of the output characteristics from the computational model may be compared to distributions of output characteristics observed in a population. Statistical quality tests may be performed on the output distributions of the computational model and the observed output distributions to ensure model integrity.

Once trained and validated, MRS process model 104 may be used to predict values of output parameters 106 when provided with values of input parameters 102. Further, processor 202 may optimize MRS process model 104 by determining desired distributions of input parameters 102 based on relationships between input parameters 102 and desired distributions of output parameters 106 (step 312).

Processor 202 may analyze the relationships between desired distributions of input parameters 102 and desired distributions of output parameters 106 based on particular applications. For example, processor 202 may select desired ranges for output parameters 106 (e.g., likelihood of cardiovascular disease, diabetics, and/or high blood pressure, etc.). Processor 202 may then run a simulation of the computational model to find a desired statistic distribution for an individual input parameter (e.g., age, sex, weight, height, exercise level, cholesterol level, blood pressure, diet, habit, etc.). That is, processor 202 may separately determine a distribution (e.g., mean, standard variation, etc.) of the individual input parameter corresponding to the normal ranges of output parameters 106. After determining respective distributions for all individual input parameters, processor 202 may combine the desired distributions for all the individual input parameters to determine desired distributions and characteristics for overall input parameters 102.

Alternatively, processor 202 may identify desired distributions of input parameters 102 simultaneously to maximize the possibility of obtaining desired outcomes. In certain embodiments, processor 202 may simultaneously determine desired distributions of input parameters 102 based on zeta statistic. Zeta statistic may indicate a relationship between input parameters, their value ranges, and desired outcomes. Zeta statistic may be represented as $$\zeta = \sum_{1}^{j} \sum_{1}^{i} |S_{ij}| \left(\frac{\sigma_i}{\bar{x}_i}\right)\left(\frac{\bar{x}_j}{\sigma_j}\right),$$

where $\bar{x}_i$ represents the mean or expected value of an ith input; $\bar{x}_j$ represents the mean or expected value of a jth outcome; $\sigma_i$ represents the standard deviation of the ith input; $\sigma_j$ represents the standard deviation of the jth outcome; and $|S_{ij}|$ represents the partial derivative or sensitivity of the jth outcome to the ith input.

Under certain circumstances, $\bar{x}_i$ may be less than or equal to zero. A value of 3 $\sigma_i$ may be added to $\bar{x}_i$ to correct such problematic condition. If, however, $\bar{x}_i$ is still equal zero even after adding the value of 3 $\sigma_i$, processor 202 may determine that $\sigma_j$ may be also zero and that the process model under optimization may be undesired. In certain embodiments, processor 202 may set a minimum threshold for $\sigma_i$ to ensure reliability of process models. Under certain other circumstances, $\sigma_j$ may be equal to zero. Processor 202 may then determine that the model under optimization may be insufficient to reflect output parameters within a certain range of uncertainty. Processor 202 may assign an indefinite large number to $\zeta$.

Processor 202 may identify a desired distribution of input parameters 102 such that the zeta statistic of the neural network computational model (i.e., MRS process model 104) is maximized or optimized. An appropriate type of genetic algorithm may be used by processor 202 to search the desired distribution of input parameters with the purpose of maximizing the zeta statistic. Processor 202 may select a candidate set of input parameters 102 with predetermined search ranges and run a simulation of MRS process model 104 to calculate the zeta statistic parameters based on input parameters 102, output parameters 106, and the neural network computational model. Processor 202 may obtain $\bar{x}_i$ and $\sigma_i$ by analyzing the candidate set of input parameters 102, and obtain $\bar{x}_j$ and $\sigma_j$ by analyzing the outcomes of the simulation. Further, processor 202 may obtain $|S_{ij}|$ from the trained neural network as an indication of the impact of the ith input on the jth outcome.

Processor 202 may select the candidate set of input parameters if the genetic algorithm converges (i.e., the genetic algorithm finds the maximized or optimized zeta statistic of MRS process model 104 corresponding to the candidate set of input parameters). If the genetic algorithm does not converge, a different candidate set of input parameters 102 may be created by the genetic algorithm for further searching. This searching process may continue until the genetic algorithm converges and a desired set of input parameters 102 is identified. Processor 202 may further determine desired distributions (e.g., mean and standard deviations) of input parameters 102 based on the desired input parameter set. Once the desired distributions are determined, processor 202 may define a valid input space that may include any input parameter within the desired distributions (step 314).

In one embodiment, statistical distributions of certain input parameters may be impossible or impractical to control. For example, an input parameter may be associated with a physical attribute of a patient, such as age, or the input parameter may be associated with a constant variable within MRS process model 104 itself. These input parameters may be used in the zeta statistic calculations to search or identify desired distributions for other input parameters corresponding to constant values and/or statistical distributions of these input parameters.

Figure 4:
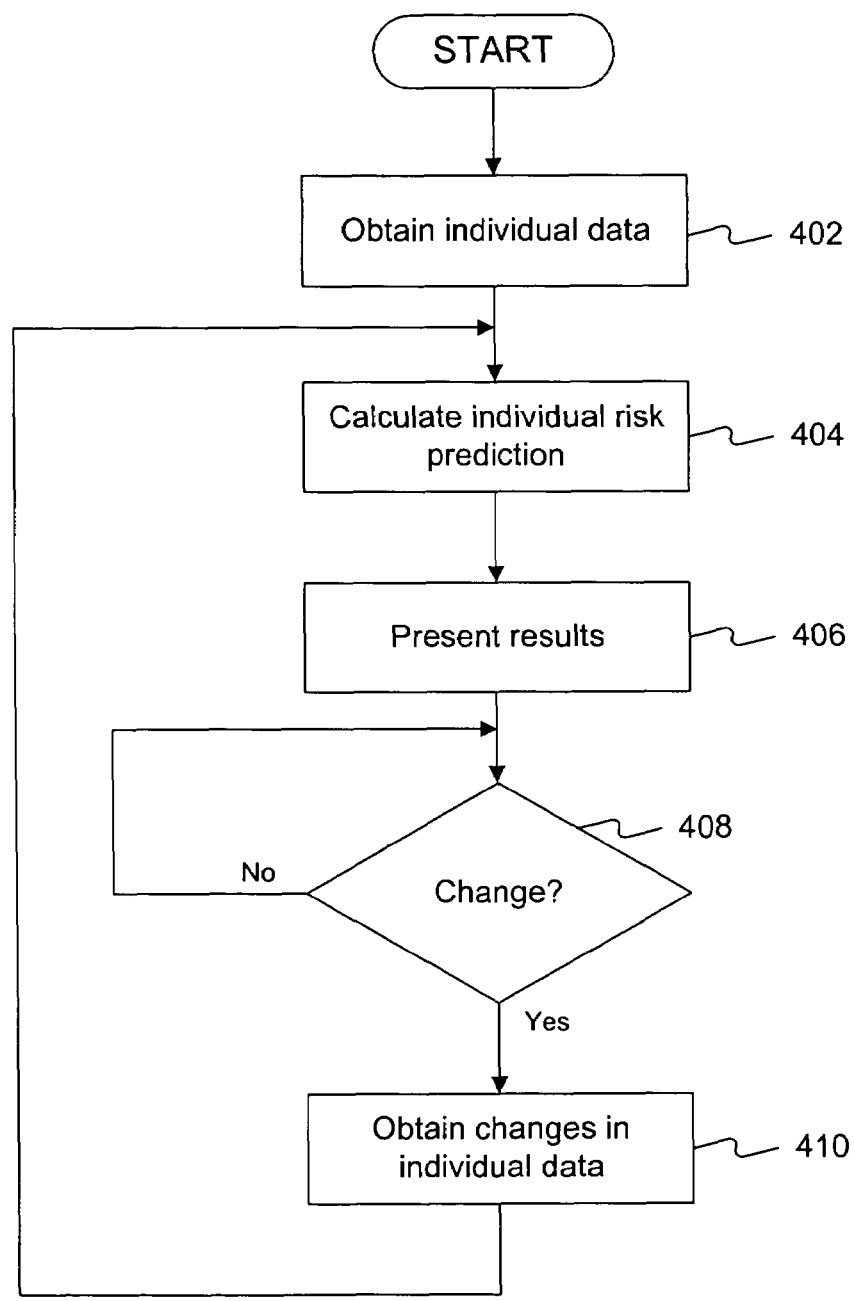
FIG. 4 shows an exemplary individual perspective process consistent with certain disclosed embodiments.

Returning to FIG. 1, after MRS process model 104 is trained, validated, and optimized, an individual user may use MRS process model to predict one or more medical risks based upon individual medical data. Processor 202 may perform an individual perspective process to provide information on medical risks to the individual user. For example, processor 202 may provide individual risk prediction 122 based on MRS process model 104 and individual data 112. FIG. 4 shows an exemplary individual perspective process performed by processor 202.

Processor 202 may obtain individual data 112 from the individual user (step 402). Processor 202 may obtain individual data 112 directly from user inputs, from a database, or from other computer systems maintaining such data. Individual data 112 may reflect any health related information about the individual user, such as age, sex, height, exercise level, cholesterol level, blood pressure, diet, particular diseases and treatments, health habit (e.g., smoking, alcohol), etc.

After obtaining individual data 112, processor 202 may calculate individual risk predication 122 based on MRS process model 104 (step 404). For example, processor 202 may calculate medical risks such as cardiovascular disease, diabetic, etc., based on input individual data 112 (e.g., age, sex, height, exercise level, cholesterol level, blood pressure, diet, particular diseases and treatments, health habit, etc.) and MRS process model 104. Processor 202 may also calculate certain other calculations related to individual data 112 and individual risk prediction 122, such as statistics about individual data 112 in comparison with input parameters 102.

Figure 5:
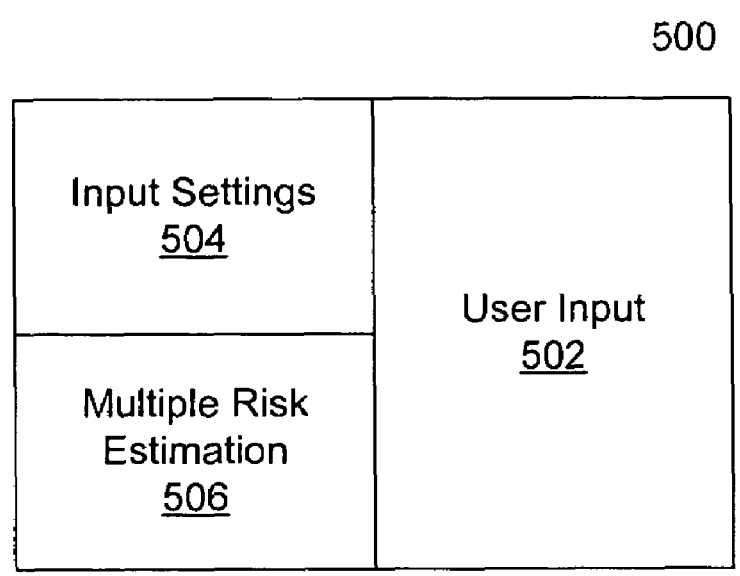
FIG. 5 shows a block diagram of an exemplary graphical user interface consistent with certain disclosed embodiments.

Processor 202 may also present individual risk prediction 122 and results of other calculation to the individual user through a user interface (step 406). The user interface may include any appropriate textual, audio, and/or visual user interface. FIG. 5 shows a block diagram of an exemplary graphical user interface (GUI) 500 on console 208.

As shown in FIG. 5, GUI 500 may include separate display areas to present different types of data. For example, GUI 500 may include a user input area 502, an input setting area 504, and a multiple risk estimation area 506. Other display areas, however, may also be used. User input area 502 may be used to accept health data input (i.e., individual data 112) from the individual user and/or to allow the user to change the values of certain inputs to observe the likely effect of such changes. In certain embodiments, slider control mechanism may be used such that the user may easily set or change the inputs. In addition, the slider control may also be used to set minimum and maximum limits for such inputs. These limits may be pre-determined or may be determined at real-time by MRS process model 104.

Input setting area 504 may be used to list values of input data 112 (e.g., such as age, sex, height, exercise level, cholesterol level, blood pressure, diet, particular diseases and treatments, and health habit, etc.). Input setting area may also show a comparison between values of individual data 112 with the overall values of input parameters 102 that are used to generate MRS process model 104. Further, multiple risk estimation area 506 may be used to present to the user how multiple risk may be related to one or more health input data. For example, multiple risk estimation area 506 may include a radar control chart to show how a particular set of inputs drive the values of multiple health risks.

Returning to FIG. 4, after processor 202 calculates individual risk prediction 122 and presents the calculation and certain other data to the user (steps 404 and 406), processor 202 may determine whether there are any changes on the values of individual data 112 (step 408). If there is no change (step 408; no), processor 202 may continue step 408 to monitor any change that may be made by the user. On the other hand, if any of individual data 112 has been changed (step 408; yes), processor 202 may obtain changed individual data 112 (step 410). Further, the individual perspective process may be continued at step 404 to calculate individual predication 122 based on the changed individual data 112.

Figure 6:
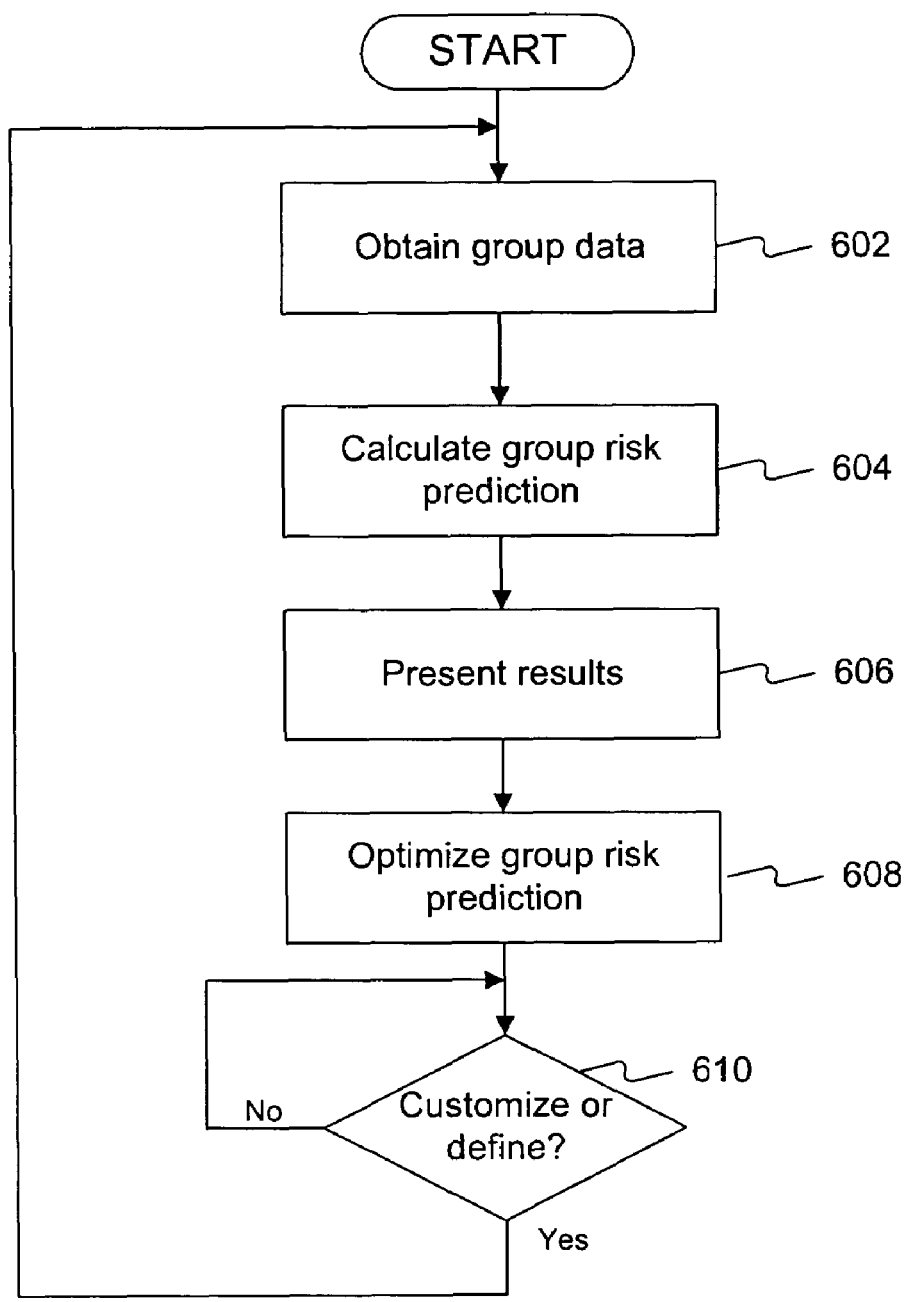
FIG. 6 shows an exemplary group perspective process consistent with certain disclosed embodiments.

Additionally or alternatively, a healthcare institution or other organization may also use MRS process model 104 to manage health care risks and/or to profile health habits of a particular population. Process 202 may perform a group perspective process to identify medical risks and their corresponding mitigation factors. For example, processor 202 may provide group risk prediction 124 based on MRS process model 104 and group data 114. FIG. 6 shows an exemplary group perspective process.

As shown in FIG. 6, processor 202 may obtain group data 114 (step 602). Processor 202 may obtain group data 114 directly from input devices 210 under the control of an administrator of computer system 200. Alternatively, processor 202 may also obtain group data 114 from a database (e.g., database 214-1, database 214-2, etc.) or from other computer systems maintaining such data. Group data 114 may reflect health related information about a particular group or population. Such health related information may include age, sex, height, exercise level, cholesterol level, blood pressure, diet, particular diseases and treatments, health habit (e.g., smoking, alcohol), etc. Further, group data 114 may include historical health data and/or user-defined health data.

After obtaining group data 114, processor 202 may calculate group risk predication 124 based on MRS process model 104 (step 604). For example, processor 202 may calculate health risks for a particular group, such as cardiovascular disease, diabetic, etc., based on group data 114 and MRS process model 104. Processor 202 may also calculate distribution data of the health risks based on group data 114 and group risk prediction 124. For example, processor 202 may calculate likelihood of a certain disease among different age group or ethnic groups. Other statistics of group data 114 and group risk prediction 124 may also be calculated. Processor 202 may also optimize (e.g., to minimize the overall health risks) group risk prediction 124 based on desired distributions of group data 114, such as desired exercise level, diet, treatments, and/or health habit, etc. Processor 202 may optimize group risk prediction 124 based on zeta statistic, as explained in above sections. A new set of values of group data 114 (i.e., optimized group data 114) may be identified to minimize a certain type of health risk. Other optimization methods, however, may also be used. For example, the administrator may define a set of values of group data 114 (i.e., user-defined group data 114) based on predetermined criteria to minimize one or more health risks.

Figure 7:
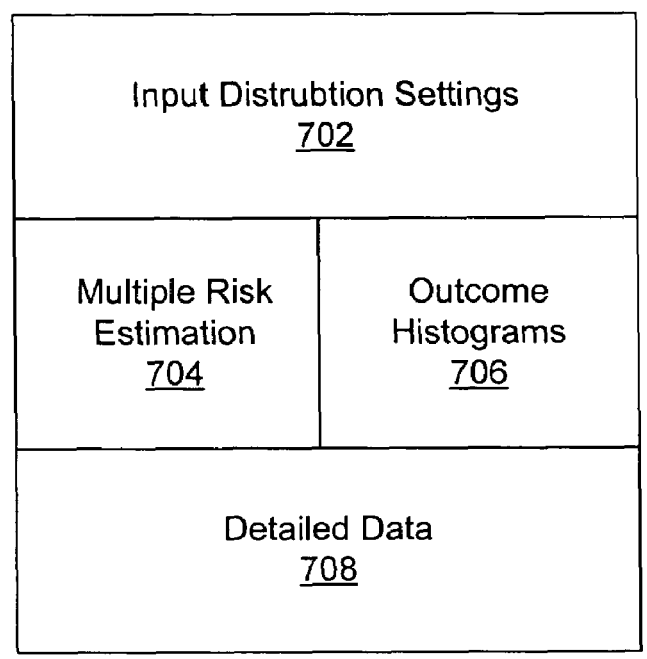
FIG. 7 shows another block diagram of an exemplary graphical user interface consistent with certain disclosed embodiments.

Processor 202 may also present the results of the group perspective process to the administrator through a user interface (step 606). Similar to the user interface provided for the individual perspective process, the user interface for group perspective process may include any appropriate user interface, such as textual (e.g., electronic mail), audio, or visual interfaces, or any combination thereof. FIG. 7 shows an exemplary graphical user interface (GUI) 700 provided on console 208.

GUI 700 may also include separate display areas to present different types of data. For example, GUI 700 may include an input data distribution settings area 702, a multiple risk estimation area 704, an outcome histogram area 706, and a detailed data area 708. Other display areas, however, may also be used.

Input data distribution settings area 702 may be used to display original group data 114, optimized group data 114, and/or user-defined group data 114. These group data (e.g., different distributions of group health information among a group or population) may also be displayed simultaneously to provide comparisons among different group data.

Multiple risk estimation area 704 may be used to display how multiple risks may be related to one or more health input data from group data 114. For example, multiple risk estimation area 704 may include a radar control chart to show how a particular set of group data drive the likelihood of multiple health risks. Further, outcome histogram area 706 may be used to show different values of group risk predication 124 respectively corresponding to original group data 114, optimized group data 114, and/or user-defined group data 114.

Detailed data area 708 may be used to display values of various data used in the group perspective process performed by processor 202, such as a spread sheet showing detailed data in calculations corresponding to group risk predication and/or optimization of group data 114, etc.

Returning to FIG. 6, processor 202 may optimize multiple health risks of group risk prediction 124 (step 608). For example, processor 202 may minimize the multiple health risks by calculating a desired set of values of group data 114. Zeta statistic may also be used in the optimization.

After processor 202 presents the results of the calculation (step 606) and the optimization (step 608), processor 202 may determine whether the administrator wants to customize or define group data 114 (step 610). If customization is not needed (step 610; no), processor 202 may continue step 610 to monitor any change that may be made by the administrator. On the other hand, if customization is needed (step 610; yes), processor 202 may proceed to step 602 to obtain changed group data 114 and continue the group perspective process.

INDUSTRIAL APPLICABILITY

The disclosed systems and methods may provide efficient and accurate medical risk stratification based on health information such as genetic, lifestyle, and/or environmental factors (both current and historical). Such technology may be used to predict and manage individual health risks as well as to analyze and manage health risks of a group or a population.

Individual users may use the disclosed systems and methods to predict potential health risks or to calculate likelihood of a possible disease based on their own health data. The individual users may also reduce the risks or the likelihood of a disease by changing relevant health data (e.g., lifestyle) corresponding to the risks or the disease.

Group or institutional users may use the disclosed systems and methods to calculate health risks among a population, such as a particular distribution among the population. The institutional users may also optimize the distribution to reduce the health risks of a population and to promote healthy lifestyle.

The disclosed systems and methods may also be extended to be used in non-medical field to predict or optimize other risks, such as financial market, etc. Parts of the disclosed system or steps of the disclosed method may be used by computer system providers to facilitate or integrate other process models.

The disclosed systems and methods may also provide an efficient solution to provide a composite MRS model to combine multiple MRS models or multiple expert knowledge bases. The combined data records may be reconciled based on a unified medical risk and thus may be used together for creating other process models. Further, the disclosed expert knowledge combination process may be used in other fields of industry as well to combine or reconcile different expert knowledge bases.

Other embodiments, features, aspects, and principles of the disclosed exemplary systems will be apparent to those skilled in the art and may be implemented in various environments and systems.

What is claimed is:

1. A computer-implemented method for a medical risk stratification (MRS) computer system, comprising:

obtaining data records associated with one or more health variables and a plurality of medical risks from a plurality of MRS models based on an expert knowledge combination process, wherein the health variables represent health information of one or more people;

establishing a medical risk process model indicative of interrelationships between the plurality of medical risks and a plurality of health parameters based on the data records;

obtaining a set of values corresponding to the plurality of health parameters;

calculating values of the plurality of medical risks simultaneously based upon the set of values corresponding to the plurality of health parameters and the medical risk process model;

optimizing the plurality of health parameters to minimize the plurality of medical risks simultaneously; and presenting the values of the plurality of medical risks via the MRS computer system.

2. The computer-implemented method according to claim 1, wherein the establishing includes:

selecting the plurality of health parameters from the one or more health variables;

generating a computational model indicative of the interrelationships;

determining desired statistical distributions of the plurality of health parameters of the computational model; and recalibrating the plurality of health parameters based on the desired statistical distributions.

3. The computer-implemented method according to claim 2, wherein selecting further includes:

pre-processing the data records; and using a genetic algorithm to select the plurality of health parameters from the one or more health variables based on a mahalanobis distance between a normal data set and an abnormal data set of the data records.

4. The computer-implemented method according to claim 2, wherein generating further includes:

creating a neural network computational model;

training the neural network computational model using the data records; and validating the neural network computation model using the data records.

5. The computer-implemented method according to claim 2, wherein determining further includes:

determining a candidate set of values of the health parameters with a maximum zeta statistic using a genetic algorithm; and determining the desired distributions of the health parameters based on the candidate set, wherein the zeta statistic $\zeta$ is represented by:

$$\zeta = \sum_{1}^{j} \sum_{1}^{i} |S_{ij}| \left(\frac{\sigma_i}{\bar{x}_i}\right)\left(\frac{\bar{x}_j}{\sigma_j}\right),$$

provided that $\bar{x}_i$ represents a mean of an ith input; $\bar{x}_j$ represents a mean of a jth output; $\sigma_i$ represents a standard deviation of the ith input; $\sigma_j$ represents a standard deviation of the jth output; and $|S_{ij}|$ represents sensitivity of the jth output to the ith input of the computational model.

6. The computer-implemented method according to claim 1, wherein the obtaining data records includes:

selecting a common medical risk among the plurality of MRS models from the plurality of medical risks, and a plurality of model variables of the plurality of MRS models;

obtaining a set of values of the plurality of model variables;

determining a plurality of values of the common medical risk respectively corresponding to the plurality of MRS models, based on the set of values;

determining a unified medical risk based on the plurality of values of the common medical risks; and creating the data records associated with the one or more health variables by combining plurality of model variables of the plurality of MRS models and the unified medical risk.

7. The computer-implemented method according to claim 6, wherein the determining the unified medical risk includes:

determining the unified medical risk as an Euclidean distance in an Euclidean space having a plurality of dimensions, respectively representing the plurality of medical risks of the plurality of MRS models.

8. The computer-implemented method according to claim 7, wherein:

provided that m is an integer representing the total number of the plurality of MRS models, and $(x_1, x_2, x_3, \ldots, x_m)$ represents the plurality of values of the common medical risk from the plurality of MRS models, respectively; and the Euclidean distance is determined as $(x_1^2 + x_2^2 + \ldots + x_m^2)^{1/2}$.

9. A computer system, comprising:

a database containing data records associating a plurality of medical risks and a plurality of health parameters; and a processor configured to:

obtain data records associated with one or more health variables and a plurality of medical risks from a plurality of MRS models based on an expert knowledge combination process;

establish a medical risk process model indicative of interrelationships between the plurality of medical risks and a plurality of health parameters based on the data records;

obtain a set of values corresponding to the plurality of health parameters;

calculate values of the plurality of medical risks simultaneously based upon the set of values corresponding to the plurality of health parameters and the medical risk process model;

optimize the plurality of health parameters to minimize the plurality of medical risks simultaneously; and present the values of the plurality of medical risks.

10. The computer system according to claim 9, wherein, to establish the medical risk process model, the processor is further configured to:

select the plurality of health parameters from the one or more health variables;

generate a computational model indicative of the interrelationships;

determine desired statistical distributions of the plurality of health parameters of the computational model; and recalibrate the plurality of health parameters based on the desired statistical distributions.

11. The computer system according to claim 9, wherein, to obtain the data records, the processor is further configured to:

select a common medical risk among the plurality of MRS models from the plurality of medical risks, and a plurality of model variables of the plurality of MRS models;

obtain a set of values of the plurality of model variables;

determine a plurality of values of the common medical risk respectively corresponding to the plurality of MRS models, based on the set of values;

determine a unified medical risk based on the plurality of values of the common medical risks; and create the data records associated with the one or more health variables by combining plurality of model variables of the plurality of MRS models and the unified medical risk.

12. The computer system according to claim 11, wherein, to determine the unified medical risk, the processor is further configured to:
determine the unified medical risk as an Euclidean distance in an Euclidean space having a plurality of dimensions, respectively representing the plurality of medical risks of the plurality of MRS models.

13. The computer system according to claim 12, wherein:
provided that m is an integer representing the total number of the plurality of MRS models, and $(x_1, x_2, x_3, \ldots, x_m)$ represents the plurality of values of the common medical risk from the plurality of MRS models, respectively; and
the Euclidean distance is determined as $(x_1^2+x_2^2+ \ldots +x_m^2)^{1/2}$.

14. The computer system according to claim 9, further includes:
one or more input devices configured to obtain the set of values corresponding to the plurality of health parameters indicative of factual and desired health information about an individual user or a population.

15. The computer system according to claim 9, further includes:
a display device configured to:
display the set of values of the plurality of health parameters in a first display area;
display statistic data corresponding to the plurality of heath parameters in a second display area; and
display the interrelationships between the plurality of health parameters and the plurality of medical risks in a third display area.

16. A computer-readable medium for use on a computer system configured to perform a medical risk stratification procedure, the computer-readable medium having computer-executable instructions for performing a computer-implemented method comprising:
obtaining data records associated with one or more health variables and a plurality of medical risks from a plurality of MRS models based on an expert knowledge combination process, wherein the health variables represent health information of one or more people;
establishing a medical risk process model indicative of interrelationships between the plurality of medical risks and a plurality of health parameters based on the data records;
obtaining a set of values corresponding to the plurality of health parameters;
calculating values of the plurality of medical risks simultaneously based upon the set of values corresponding to the plurality of health parameters and the medical risk process model;
optimizing the plurality of health parameters to minimize the plurality of medical risks simultaneously; and
presenting the values of the plurality of medical risks via the computer system.

17. The computer-readable medium according to claim 16, wherein the establishing includes:
selecting the plurality of health parameters from the one or more health variables;
generating a computational model indicative of the interrelationships;
determining desired statistical distributions of the plurality of health parameters of the computational model; and
recalibrating the plurality of health parameters based on the desired statistical distributions.

18. The computer-readable medium according to claim 17, wherein determining further includes:
determining a candidate set of values of the health parameters with a maximum zeta statistic using a genetic algorithm; and
determining the desired distributions of the health parameters based on the candidate set,
wherein the zeta statistic $\zeta$ is represented by:

$$\zeta = \sum_{1}^{j} \sum_{1}^{i} |S_{ij}| \left(\frac{\sigma_i}{\bar{x}_i}\right)\left(\frac{\bar{x}_j}{\sigma_j}\right),$$

provided that $\bar{x}_i$ represents a mean of an ith input; $\bar{x}_j$ represents a mean of a jth output; $\sigma_i$ represents a standard deviation of the ith input; $\sigma_j$ represents a standard deviation of the jth output; and $|S_{ij}|$ represents sensitivity of the jth output to the ith input of the computational model.

19. The computer-readable medium according to claim 18, wherein the obtaining data records includes:
selecting a common medical risk among the plurality of MRS models from the plurality of medical risks, and a plurality of model variables of the plurality of MRS models;
obtaining a set of values of the plurality of model variables;
determining a plurality of values of the common medical risk respectively corresponding to the plurality of MRS models, based on the set of values;
determining a unified medical risk based on the plurality of values of the common medical risks; and
creating the data records associated with the one or more health variables by combining plurality of model variables of the plurality of MRS models and the unified medical risk.

* * * * *